United States Patent [19]
Nardella

[11] Patent Number: 5,665,085
[45] Date of Patent: Sep. 9, 1997

[54] ELECTROSURGICAL CUTTING TOOL

[75] Inventor: Paul C. Nardella, North Easton, Mass.

[73] Assignee: Medical Scientific, Inc., Taunton, Mass.

[21] Appl. No.: 285,413

[22] Filed: Aug. 3, 1994

Related U.S. Application Data

[63] Continuation of Ser. No. 5,006, Jan. 15, 1993, abandoned, which is a continuation-in-part of Ser. No. 786,572, Nov. 1, 1991, abandoned.

[51] Int. Cl.$^6$ .................................................. A61B 17/39
[52] U.S. Cl. ........................... 606/41; 606/46; 606/48; 606/142; 227/180.1
[58] Field of Search .................................. 606/32, 37, 39, 606/40, 41, 142, 143, 167, 171, 172, 45–50; 227/175.1, 176.1, 180.1, 901, 902

[56] References Cited

U.S. PATENT DOCUMENTS

| | | | |
|---|---|---|---|
| 1,683,708 | 9/1928 | Wappler et al. | 128/303.16 |
| 1,881,250 | 10/1932 | Tomlinson | 606/50 |
| 2,031,682 | 11/1936 | Wappler et al. | 174/89 |
| 2,068,721 | 11/1937 | Wappler et al. | 28/303.15 |
| 3,768,482 | 10/1973 | Shaw . | |
| 3,826,263 | 7/1974 | Cage et al. . | |
| 3,952,748 | 4/1976 | Kaliher et al. | 606/34 |
| 4,038,984 | 8/1977 | Sittner . | |
| 4,043,342 | 8/1977 | Morrison, Jr. | 606/50 |
| 4,161,940 | 7/1979 | Does et al. . | |
| 4,228,800 | 10/1980 | Degler, Jr. et al. . | |
| 4,334,539 | 6/1982 | Childs et al. | 606/34 |
| 4,353,371 | 10/1982 | Cosman . | |
| 4,534,347 | 8/1985 | Taylor . | |
| 4,651,734 | 3/1987 | Does . | |
| 4,655,216 | 4/1987 | Tischer | 128/303.17 |
| 4,674,498 | 6/1987 | Stasz . | |
| 4,712,544 | 12/1987 | Ensslin . | |
| 4,784,137 | 11/1988 | Kulik et al. | 606/142 |
| 4,815,465 | 3/1989 | Alvarado | 606/164 |
| 4,931,047 | 6/1990 | Broadwin et al. . | |
| 5,013,312 | 5/1991 | Parins et al. . | |
| 5,389,098 | 2/1995 | Tsuruta et al. | 606/41 |
| 5,403,312 | 4/1995 | Yates et al. | 606/50 |

FOREIGN PATENT DOCUMENTS

| 1459659 | 2/1989 | U.S.S.R. | 606/139 |

OTHER PUBLICATIONS

New Medical Archive, First Issue (The 211th) Jan.–Feb. 1958, Vittenberger.

Vittenberger, "*Instrument for Stomach Resection and Bowel Anastomosis Used During Closed Procedures*", New Surgical Archive, Ministry of Health of the Ukraine Soviet Socialist Republic (Jan.–Feb. 1958).

*Primary Examiner*—Lee S. Cohen
*Assistant Examiner*—Michael Peffley
*Attorney, Agent, or Firm*—Nutter, McClennen & Fish, LLP

[57] ABSTRACT

An electrosurgical tool comprises a retractable cutting element moveable along a linear cutting path and an electrical energy supply source which communicates electrical energy (e.g., radio frequency energy) through the cutting element and to tissue adjacent the cutting element. The cutting element may be formed of a sharp or non-sharpened material. During surgical procedures the electrosurgical cutting device is able to simultaneously cut tissue and cauterize, or fuse, the tissue in areas adjacent the incision through the application of electrical energy. The effect is a reduced amount of bleeding associated with surgical procedures and an enhanced ability to control and eliminate bleeding. Optionally, the electrosurgical cutting device may also include a supply of surgical staples which are deployed simultaneously with the cutting action and delivery of electrosurgical energy to adjacent tissue.

29 Claims, 5 Drawing Sheets

ELECTROSURGICAL CUTTING TOOL

REFERENCE TO RELATED APPLICATIONS

This is a continuation of application Ser. No. 08/005,006, filed on Jan. 15, 1993 (abandoned), which is a continuation-in-part of Ser. No. 07/786,572, filed Nov. 1, 1991 (abandoned).

BACKGROUND OF THE INVENTION

The present invention relates to an electrosurgical tool which is adapted to simultaneously cut, fuse, and cauterize the cut tissue so as to improve hemostasis.

Surgical procedures often require incisions to be made in internal organs, such as the intestine, causing profuse bleeding at the site of the incision. Prompt control or elimination of the bleeding is of paramount importance to the success and safety of the procedure.

Currently known surgical cutting devices utilize different techniques to control or eliminate bleeding. One known device is the Proximate Linear Cutter available from the Ethicon, Inc. of Somerville, N.J. This device is specifically adapted to make an incision in tissue or an organ such as the intestine. The device engages a portion of the tissue or organ between two tyne-like members. To effect cutting, a blade mounted on one of the tynes travels along a predetermined path, thereby making a linear incision through the tissue or organ. Simultaneously, surgical staples are deployed by the cutting device on either side of the incision, resulting in the separation of the organ into two segments, each of which is sealed adjacent to the incision by surgical staples. Despite the use of surgical staples and the precise cutting of the tissue, bleeding is not entirely eliminated and separate cauterization procedures must often be utilized to control or stop bleeding.

Surgical devices also are known which utilize electrical current in the form of radio frequency (RF) energy to cauterize tissue and to prevent or control bleeding. U.S. Pat. No. 4,651,734 discloses a surgical scalpel modified to include an electrode. This scalpel has the ability to cut tissue and, when properly positioned, to cauterize tissue following a cutting procedure. Such a surgical tool is useful but does not simultaneously cut and cauterize tissue. The separate cauterization procedure which must be utilized is relatively time consuming and may result in unnecessary bleeding. Moreover, such a scalpel is not well suited to many surgical procedures such as the transection of the intestine.

Accordingly, there is a need for a surgical tool which conveniently and safely enables precise incisions to be made in internal organs, and which simultaneously is able to eliminate essentially all bleeding which results from the incision.

It is thus an object of the invention to provide a surgical tool which has improved cutting capability and which decreases some of the risk associated with surgery by minimizing the amount of bleeding resulting from incisions. Another object is to provide a surgical tool which is adapted to simultaneously cut tissue and to cauterize the cut tissue. A further object is to provide an electrosurgical tool which is specifically adapted to make linear incisions in internal organs and, simultaneously, to fuse the tissue adjacent to the incision in order to eliminate any associated bleeding. It is also an object of the invention to provide such a surgical device that does not require a sharpened surgical blade to sever tissue. Other objects of the invention will be apparent upon reading the disclosure which follows.

SUMMARY OF THE INVENTION

The present invention comprises an electrosurgical cutting tool which is able to effect a precise incision through tissue, while at the same time ensuring that essentially all of the bleeding which results from the incision is controlled or eliminated. The electrosurgical cutting tool features a housing which includes a handle portion and a cutting template element which is disposed adjacent to the handle portion of the housing. The cutting template preferably includes first and second elongate tyne elements which define a tissue engaging space. A first tyne element includes a retractable cutting element which is adapted to travel along a linear cutting path defined within the first tyne. The cutting element is electrically insulated from the remainder of the tool and is in electrical communication with an active electrode which provides a source of electrosurgical energy to the blade. The surgical cutting tool of the invention also includes a mechanism, preferably located on the handle, which controls the movement of the cutting element along the cutting path.

The electrosurgical cutting tool may be a bipolar device or a monopolar device. In the preferred bipolar configuration an active electrode supplies electrical current to the cutting element, and a return electrode is disposed on a tissue-contacting portion of the second tyne. A return electrode is not integrally associated with the tool when it is configured as a monopolar device. Instead, a ground plate, remote from the tool itself, is positioned to contact a portion of the patient's body.

The cutting element can be a sharpened blade, an electrode wire, a conductive material, or a conductive coating formed on a non-conductive substrate. The cutting element does not necessarily require a level of sharpness typically associated with conventional surgical cutting tools.

The delivery of electrosurgical energy through the cutting element, whether a sharpened blade or not, enhances, the cutting performance and more importantly, facilitates cauterization and/or fusion of the tissue following the incision. It has been found that the use of radio frequency energy in connection with the cutting tool effectively allows the simultaneous cutting, cauterizing and fusing of tissue adjacent the incision in order to eliminate virtually all resulting bleeding.

In another embodiment of the invention a plurality of surgical staples may be deployed by the device during a cutting procedure. In this embodiment a surgical staple cartridge is disposed within the first tyne, defining a central longitudinal groove through which the cutting element is able to travel. The surgical staple cartridge includes a plurality of staples, preferably disposed in dual rows on either side of the longitudinal groove. Upon movement of the cutting element, a staple ejecting device travels with the element along the length of the staple cartridge causing the staples to be deployed through the tissue. A staple closing anvil preferably is disposed in the second tyne to effect closure of the staples. This embodiment is advantageous as it allows the tissue to be cut, and at the same time, enables a row of staples to be deployed adjacent the incision while electrical current is passed through the cutting element to eliminate bleeding by effecting cauterization and tissue fusion. In some instances it may be desirable to deliver electrosurgical energy through the surgical staples as well as through the cutting element.

DETAILED DESCRIPTION OF THE INVENTION

Figure 1:
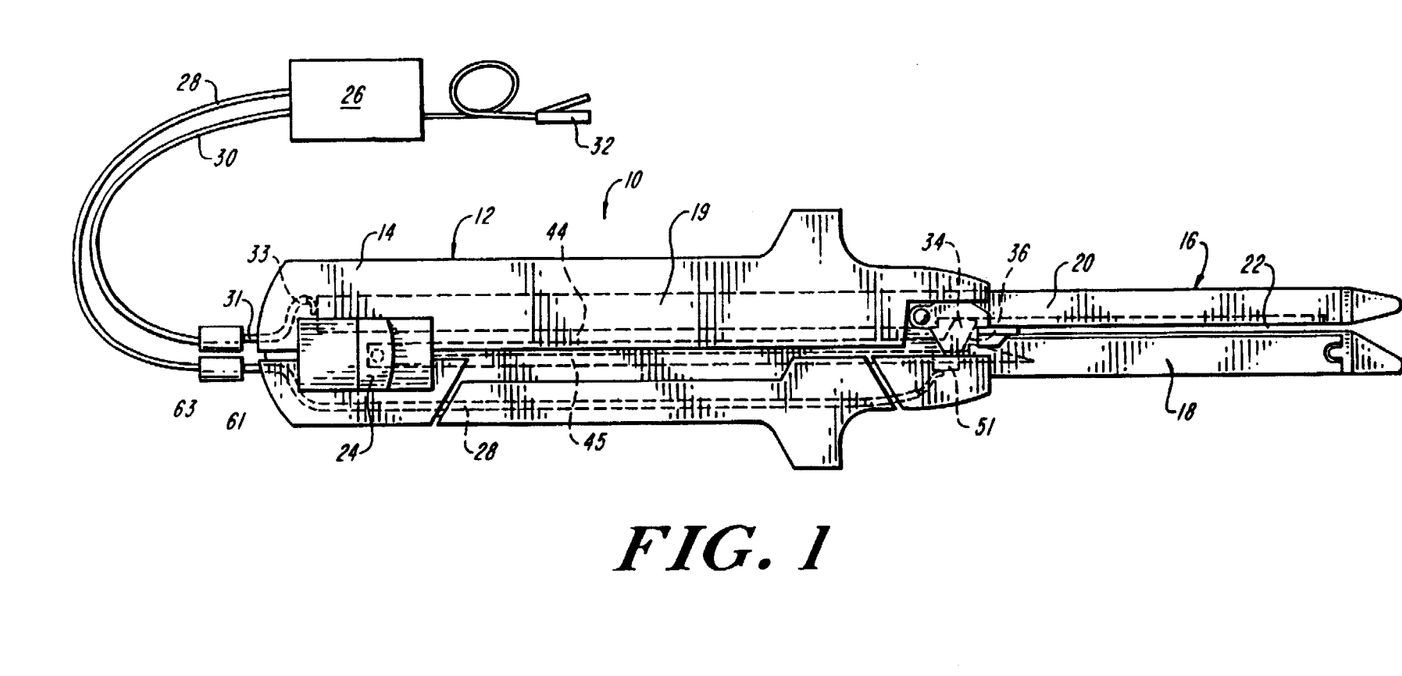
FIG. 1 schematically illustrates the surgical cutting tool of the invention, including a supply source of electrosurgical energy.
Figure 2:
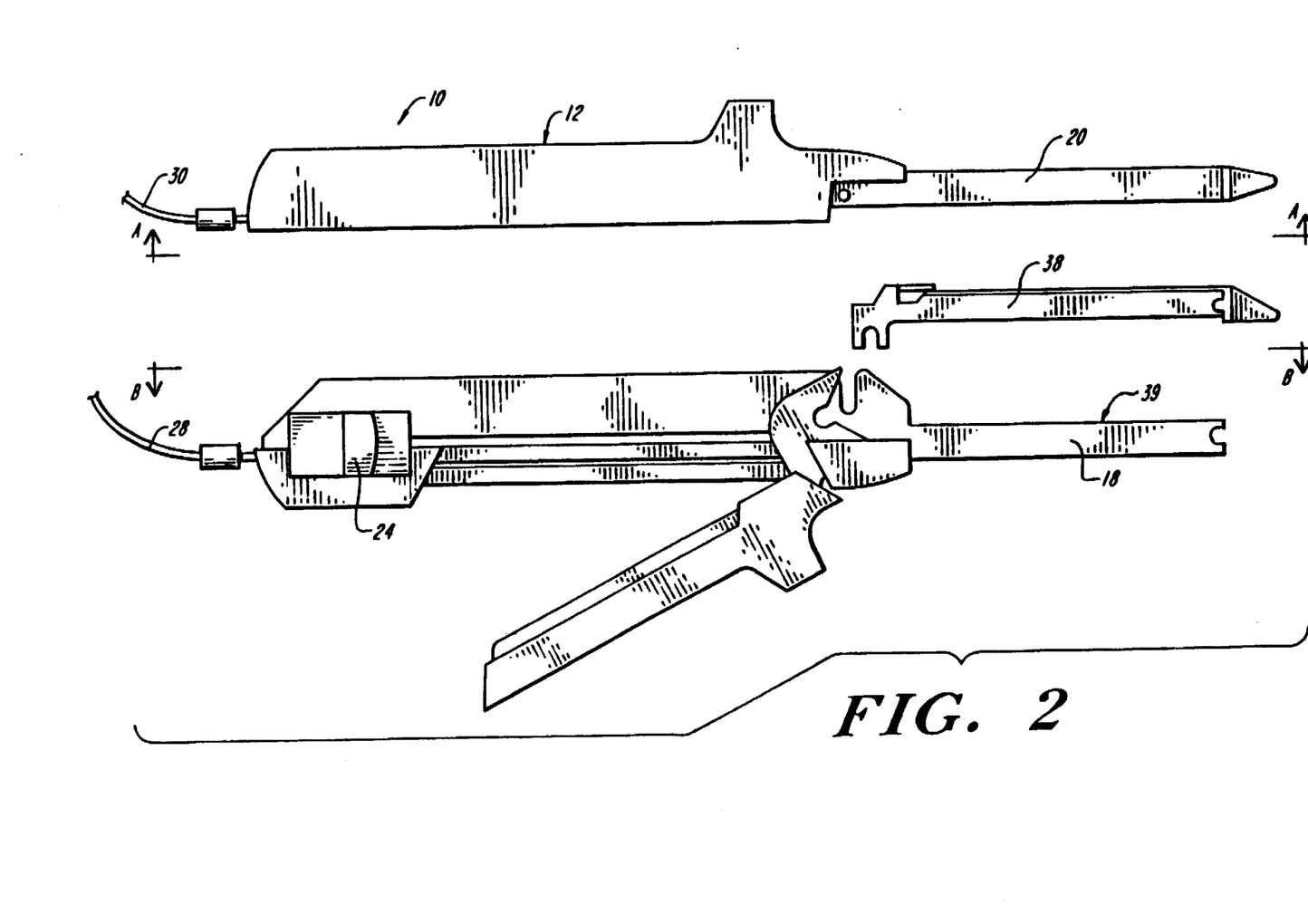
FIG. 2 is an exploded side view of the electrosurgical cutting tool illustrated in FIG. 1.

FIGS. 1 and 2 illustrate one embodiment of the invention in which the surgical cutting tool 10 comprises a housing 12 including a handle portion 14. Adjacent handle portion 14 is cutting template element 16 which includes a first tyne 18 and a second tyne 20. The two tynes 18, 20 of cutting template element 16 are substantially parallel and define a tissue engaging space 22 into which is inserted the tissue or organ to be incised. In a preferred embodiment, the surgical tool 10 includes a lever 24 which facilitates the movement of a cutting element 35, e.g., a blade 34, along a predetermined path.

FIG. 1 further illustrates an electrosurgical generator 26 which serves as an energy source from which electrical current, preferably in the radio frequency range, is communicated to the cutting tool through insulated wire 28. Insulated wire 30 communicates through connector 31 and internal ground wire 33 with a conductive portion of tyne 20 which serves as a ground. A control switch 32, preferably in the form of a foot petal, may be used to control the power supplied to the cutting tool. Alternatively, a control switch may be disposed on a portion of the cutting tool such as the housing 12.

Figure 3:
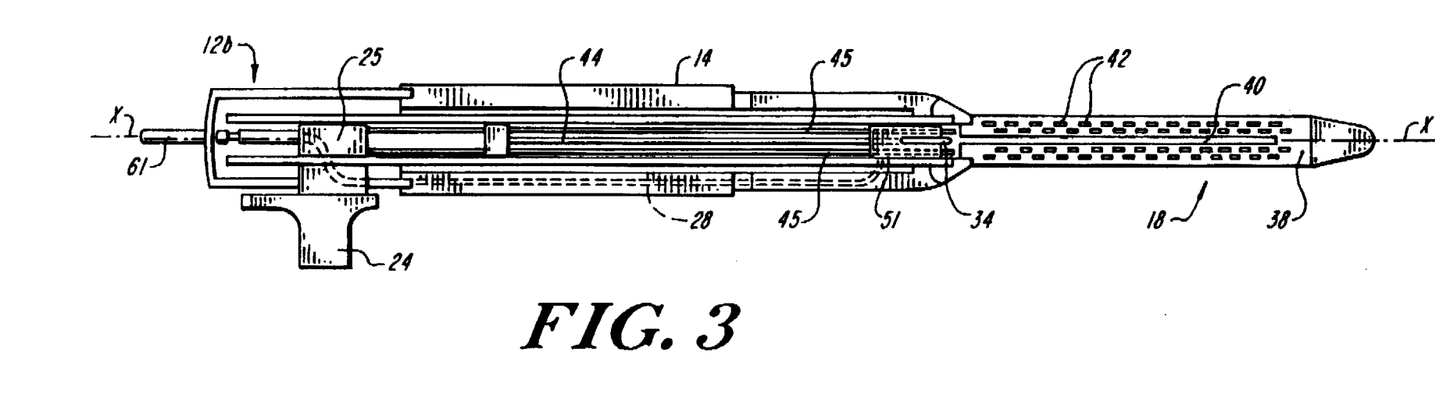
FIG. 3 is a sectional view of the electrosurgical tool of FIG. 2 at lines A—A.

As best shown in FIGS. 1 and 3, blade 34 can be retracted when not in use. In the retracted position blade 34 is disposed rearward of the first tyne 18 within a forward portion of housing 12. Blade 34 includes a cutting edge 36 disposed at the leading edge of the blade. Further, a blade actuation arm 44 which extends into housing 12 is either attached to or integral with blade 34. The blade 34 is adapted to move along the longitudinal axis x of the tyne 18 upon actuation of lever 24 in order to effect the cutting of tissue.

A surgical staple cartridge 38 may optionally be seated within the first tyne 18, as illustrated in FIGS. 1 through 3. Cartridge 38 is adapted to securely fit within a channel 39 formed in tyne 18. The staple cartridge 38 includes a central cutting groove 40 through which the cutting blade 34 passes during a cutting procedure. Dual rows of openings 42 through which surgical staples (not shown) emerge straddle either side of groove 40.

As further illustrated in FIGS. 1 and 3, lever 24 preferably is connected to the blade 34 through an actuation arm 44. Forward movement of lever 24 thus effects movement of the blade 34 causing it to traverse the cutting groove 40. Preferably, a staple ejecting mechanism, such as ejection arms 45, is actuated simultaneous with actuation of the blade. In this way staples are ejected through openings 42 as the blade traverses the groove 40. As shown in the illustrated embodiment lever 24 may be connected to ejection arms 45 such that movement of the lever 24 also controls movement of the ejection arms 45.

Figure 5:
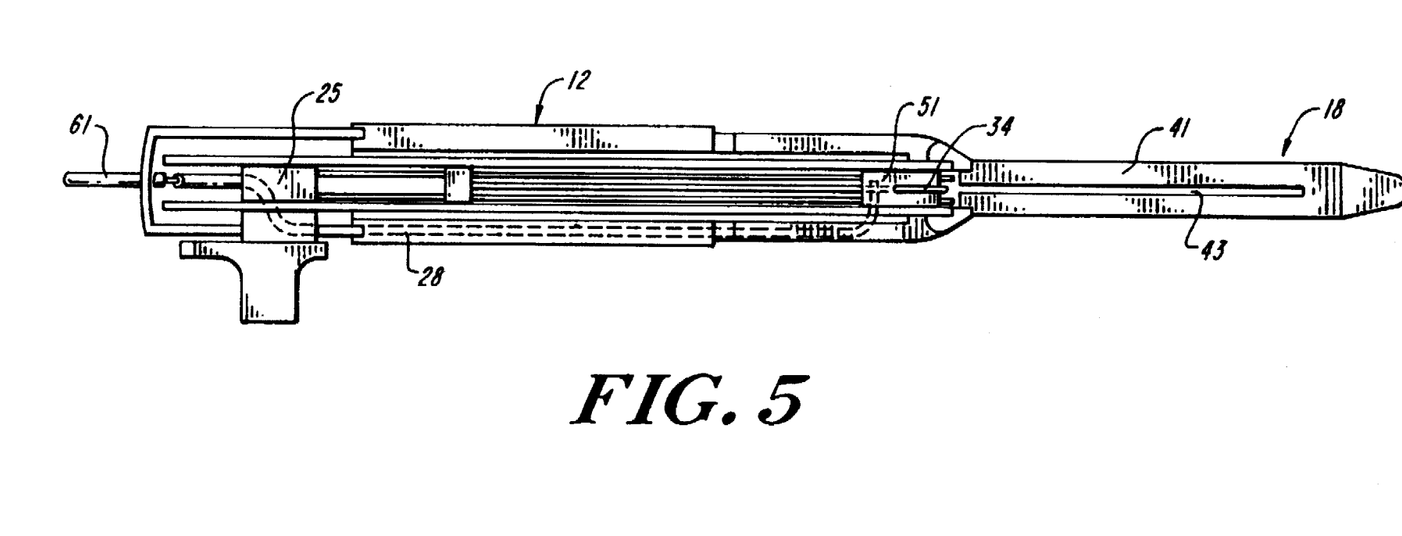
FIG. 5 is a sectional view of the electrosurgical tool of FIG. 2 at lines B—B in an embodiment which does not include a surgical staple cartridge.

FIG. 5 illustrates an embodiment of the invention in which the electrosurgical cutting tool does not utilize surgical staples. In this embodiment the tissue contacting surface 41 of tyne 18 is constructed of or coated with a non-conducting material, such as a suitable polymer. Surface 41 defines a cutting groove 43 through which blade 34 travels when it effects a cutting procedure.

Figure 4:
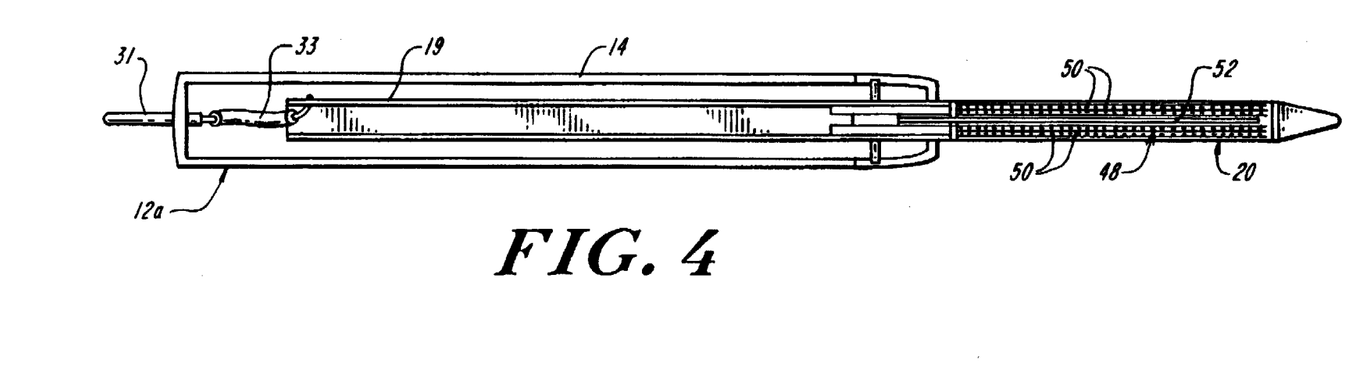
FIG. 4 is a sectional view of the electrosurgical tool of FIG. 2, at lines B—B.

As shown in FIG. 4, tyne 20 is secured within housing segment 12a which preferably is detachable from housing segment 12b associated with tyne 18. Further, tyne 20 has a tissue-contacting surface 48 which faces first tyne 18. A central groove 52 is formed in surface 48, superimposable with cutting grooves 40 or 43 of tyne 18, to facilitate movement of the blade along longitudinal axis x.

In an embodiment in which surgical staples are to be deployed simultaneously with a cutting procedure, staple cartridge 38 is present within tyne 18. In addition, surface 48 of tyne 20 includes an anvil with a plurality staple-closing depressions 50 which correspond to the openings 42 in staple cartridge 38. Preferably, dual rows of depressions are disposed on either side of groove 52. In an embodiment in which a staple cartridge is not utilized, the surface 48 may be substantially smooth and absent depressions 50. In either embodiment, however, surface 48 of tyne 20 should be made of a conductive material so that it may serve as a return electrode for electrical energy delivered through the cutting blade.

In some instances, it may be desirable to apply electrosurgical energy through the surgical staples as well as through blade 34. One skilled in the art could easily modify the electrosurgical surgical tool described herein by connecting internal wire 28 to the staple ejection arms 45 as well as to the blade 34.

FIGS. 1 through 5 illustrate the connection of the cutting tool 10 to electrosurgical generator 26. As illustrated, an inner wire 28 extends between conductive bushing 51 and electrical connector 61 which protrudes from housing 12. Insulated wire 28 may be attached to electrical connector 61 through connector 63. Bushing 51 communicates electrical current from the generator 26 to blade 34, directly or through blade actuation arm 44. In a preferred embodiment arm 44 and blade 34 are able to slide within bushing 51 while maintaining electrical contact therewith.

Figure 6A:
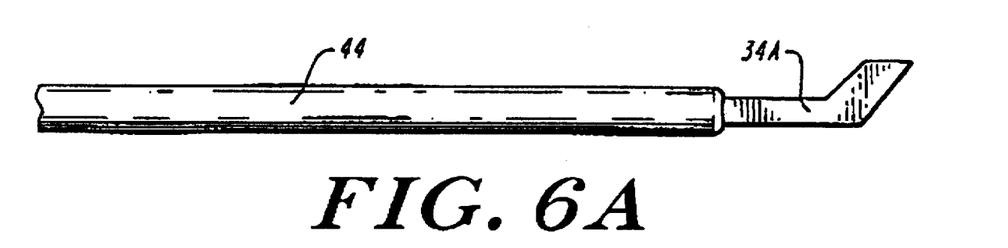
FIG. 6A is a schematic depiction of a cutting element of another embodiment of the invention.
Figure 6B:
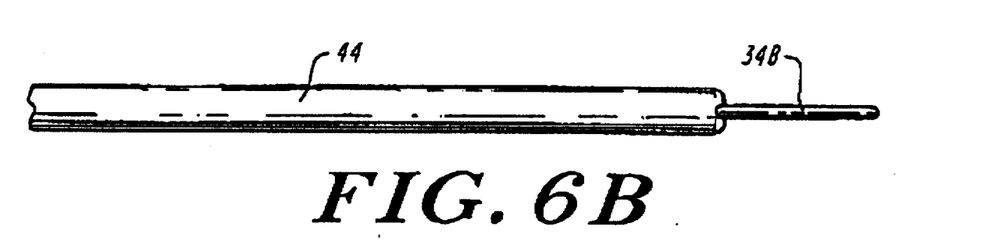
FIG. 6B is a schematic depiction of a cutting element of another embodiment of the invention.

FIGS. 6A and 6B illustrate additional embodiments of the cutting element 35. Illustrated in FIG. 6A is a cutting blade 34A, similar to blade 34 described above. The blade 34A is attached to the blade actuating arm 44 to effect movement of the blade 34A through the cutting groove 40. Blade 34A may be formed from a conductive metal, as is blade 34, but need not have a sharpened edge. The blade 34A may also be formed of a non-conductive substrate onto which a conductive coating is applied. The substrate can be composed of a non-conductive, non-sharpened material, such as a non-conductive metal, plastic or ceramic, which is coated with a conductive material, for example, a conductive metal or conductive non-metals such as suitable polymers or ceramics. As noted, blade 34A need not be sharpened as the delivery of electrosurgical energy thereto enables blade 34A to sever tissue in a manner at least as effective as a conventional, sharpened blade.

FIG. 6B depicts another embodiment of the cutting element 35 in which an electrode wire 34B is operatively associated with the actuating arm 44. Electrosurgical energy can be communicated to the wire 34B directly from wire 28 or through conductive bushing 51. Once electrical current is supplied to the wire 34B, and the actuating arm 44 and wire 34B are actuated, the wire 34B simultaneously cuts and cauterizes the biological tissue located within the tissue engaging space 22. The wire 34B can be constructed of a variety of materials known to those of ordinary skill in the art. Typically, wire 34A has a conductive core wrapped in an insulating sheath.

In a preferred embodiment, the electrosurgical cutting tool 10 of the invention comprises a bipolar cutting tool in which the cutting element 35 is electrically isolated from the remainder of the tool and serves as an electrode to deliver electrosurgical energy to the tissue. In this embodiment tyne 20 serves as the return or ground electrode. In other embodiments, it is possible that the surgical tool may comprise a monopolar tool in which electrosurgical energy is delivered through the cutting element 35, and a separate ground plate (not shown) serves as the return electrode.

In the preferred bipolar mode, surface 48 of tyne 20 serves as a ground electrode. Accordingly, exterior ground wire 30 communicates with internal ground wire 33 through connector 31. Internal ground wire 33, in turn, is in electrical communication with a conductive internal anchoring component 19 of tyne 20. Where the cutting device is used in the monopolar mode, external ground wire 30 should not electrically communicate with tyne 20, and the tissue contacting surface 48 of tyne 20 should be made from or coated with a non-conductive material.

As noted above, generator 26 supplies electrosurgical energy to the cutting element. Virtually any generator which provides electrosurgical energy for medical applications may be used with the present invention. Preferably, the generator is a voltage determinative, low source impedance generator which provides radio frequency energy. Preferably, a suitable generator can supply up to 2 amps of current and has an impedance value of less than 10 ohms.

The energy supplied by generator 26 to the electrosurgical cutting device is preferably in the radio frequency range. Although virtually any frequency in the RF range may be supplied to the cutting device, the preferred frequency range is about 100 to 1,000 KHz.

The energy requirements of the electrosurgical tool of the present invention are dynamic and depend to a great extent upon the impedance values of the tissue encountered by the blade during cutting procedures. The impedance of tissue varies among tissue types and the amount of blood present in or around the tissue. The amount of current delivered by the tool to the tissue is a function of the impedance of the tissue. Where tissue contacted has a lower impedance value, more current will be delivered to the tissue by the cutting element, and, conversely, less current will be delivered to tissue having a higher impedance value. Generally, the amount of current delivered to tissue ranges between about 0.5 and 2.0 amps. The voltage applied to the tissue between the blade and the return electrode typically is between about 50 to 100 volts rms.

The surgical tool of the present invention is particularly well adapted for use in surgical procedures which require transection of an organ such as the intestine. In operation, the tissue (e.g., intestine) is placed within space 22 defined by tynes 18 and 20. The blade is moved forward along the longitudinal axis x of tynes 18 and 20 by movement of lever 24. As the blade moves forward, it passes through the tissue causing it to be severed. Simultaneously, electrical energy (e.g., radio frequency energy), which may be activated for example by foot switch 32, is delivered to the tool. The electrosurgical current is communicated from the cutting element 35 to the tissue adjacent the element and in the vicinity of the incision.

During a cutting procedure the cutting element should be actuated such that it requires approximately 1.5 to 4.5 seconds to move along its predetermined path to sever tissue. Current should be delivered through the element to the tissue during the entire cutting procedure.

The application of electrical energy in this manner provides two advantages. Electrosurgical energy is delivered through the cutting element to adjacent tissue to allow for more effective cutting action, and to promote cauterization and/or tissue fusion which effectively eliminates all or substantially all bleeding which results from the incision. The cauterization and/or fusion effect imparted to tissue minimizes blood loss and increases the safety of the surgical procedure as cauterization occurs at substantially the same time that the incision is made.

In a preferred embodiment of the invention, the electrosurgical tool also includes a staple cartridge 38 which houses a supply of surgical staples to be supplied adjacent the incision. The staples may be deployed in one or more linear rows on either side of the incision to assist in closing the incision and sealing the severed end of the organ. The staples are deployed with the severing action of the cutting element and the tissue fusion effect imparted by the electrical energy.

One skilled in the art will appreciated that a variety of materials are well suited for the manufacture of the electrosurgical tool of this invention. For example, housing 12 and cartridge 38 may be made from or coated with various non-conducting polymers. The conductive components of the tool may be made of various metals, including surgical grade stainless steel and aluminum.

Although the invention is described with respect to the cutting tool illustrated in FIGS. 1 through 5, it is understood that various modifications may be made to the illustrated electrosurgical cutting device without departing from the scope of the invention. For example, a variety of blade actuation mechanisms may be used. Also, it is not necessary that tynes 18 and 20 take on the shape and orientation illustrated in the drawings. Moreover, the electrical connection between the generator may be made in ways other than those illustrated and described herein. Furthermore, the cutting element 35 may include both sharpened and non-sharpened elements. For example, the cutting element 35 may be a sharpened blade 34 or an electrically conductive wire 34B or substrate 34A. Thus, the present invention is potentially applicable to virtually all electrosurgical cutting devices in which a cutting element, moveable along a predetermined path, provides electrosurgical energy to incised tissue simultaneously with the cutting of tissue.

What is claimed is:

1. An electrosurgical device, comprising:

a proximal handle region;

a distal, tissue affecting portion including opposed first and second tissue engaging surfaces;

a tissue contacting, electrically isolated energy delivering electrode provided on one of the first or second tissue engaging surfaces;

a tissue contacting return electrode provided on one of the first or second tissue engaging surfaces, the return electrode being electrically isolated from the energy delivering electrode;

one or more surgical staples, provided on one of the first or second tissue engaging surfaces of the tissue affecting portion;

a driver means for deploying the staples;

means for effecting closure of one or more of the surgical staples, the means for effecting closure being provided on one of the first or second tissue engaging surfaces opposite the surgical staples; and electrosurgical current delivery means for communicating electrical energy through the energy delivering electrode to tissue to effect cutting and/or cauterization of tissue.

2. The device of claim 1 further comprising a cutting element provided on one of the first or second tissue engaging surfaces.

3. The device of claim 2 wherein the cutting element is a cutting blade that is adapted to be manipulated to sever tissue.

4. The device of claim 2 wherein the cutting element is the energy delivering electrode.

5. The device of claim 1 wherein the surgical staples are disposed within a cartridge means for housing the surgical staples, the cartridge means being provided on one of the first or second tissue engaging surfaces of the tissue affecting portion.

6. The device of claim 1 wherein the return electrode is the means for effecting closure of the surgical staples.

7. The device of claim 6 wherein the energy delivering electrode is provided on the cartridge means and is in electrical communication with the surgical staples to be deployed.

8. The device of claim 1 wherein the energy delivering electrode is the driver means.

9. The device of claim 1 wherein the voltage of the electrosurgical energy delivered to the tissue from the cutting blade is in the range of about 50 to 100 volts RMS.

10. An electrosurgical cutting device, comprising:

a tool housing including a handle portion;

a cutting portion, adjacent the handle portion, having substantially parallel first and second elongate tyne elements which define a tissue engaging space therebetween;

a pathway within the first tyne member which defines a cutting path;

a moveable curing element, electrically isolated from the remainder of the tool, said cutting element being adapted to move from a retracted position through the pathway in the first tyne to sever tissue;

means for moving the cutting element through the pathway to effect cutting of tissue;

selectively operable electrosurgical current supply means for communicating electrical energy through the cutting element to tissue to cauterize tissue simultaneous with the cutting action of the element; and a tissue contacting return electrode in electrical communication with the second tyne element and electrically isolated from the cutting element, forming a bipolar electrosurgical cutting device.

11. The device of claim 10 wherein the cutting element is a cutting blade.

12. The device of claim 10 wherein the cutting element comprises an electrode wire.

13. The device of claim 10 wherein the cutting element is selected from the group consisting of conductive metals, conductive polymers and conductive ceramics.

14. The device of claim 10 wherein the cutting element comprises a non-conductive substrate coated with a conductive material selected from the group consisting of metals, polymers and ceramics.

15. The device of claim 14 wherein the non-conductive substrate is selected from the group consisting of a non-conductive polymer or ceramic.

16. The device of claim 10, further comprising:

a cartridge means for housing a plurality of surgical staples, said cartridge means disposed on the first tyne member, on a side thereof facing the second tyne member and having a longitudinal groove therein to accommodate passage of the cutting element;

a means for deploying the staples substantially simultaneously with the cutting action of the element; and anvil means for effecting closure of the staples, the anvil means being disposed on a side of the second tyne member facing the first tyne member.

17. The device of claim 16 wherein the return electrode is in electrical communication with the anvil means, forming a bipolar electrosurgical device.

18. A method of conducting electrosurgical procedures, comprising the steps of:

providing a bipolar electrosurgical cutting tool having as an active, energy delivering electrode a retractable cutting element selectively moveable along a predetermined cutting path, said cutting element being connected to one pole of a bipolar generator and being electrically isolated from a tissue contacting return electrode disposed on a cutting portion of the tool and adjacent the cutting element;

placing tissue in the cutting path of the cutting element;

activating the cutting element such that it passes through and severs the tissue;

providing electrosurgical energy through the cutting element to tissue adjacent the incision simultaneously with the severing of tissue by the element such that the affected tissue is cauterized and bleeding associated with the incision is essentially eliminated; and deploying a plurality of surgical staples adjacent the incision, simultaneous with the steps of activating the cutting element and providing electrosurgical energy through the element to the tissue.

19. The method of claim 18, further comprising the step of deploying a plurality of surgical staples adjacent the incision, simultaneous with the steps of activating the cutting element and providing electrosurgical energy through the element to the tissue.

20. The method of claim 18 wherein the current of the electrosurgical energy delivered to tissue through the cutting element is in the range of 0.5 to 2.0 amps.

21. The method of claim 18 wherein the voltage of the electrosurgical energy delivered to tissue through the cutting element is in the range of about 50 to 100 volts RMS.

22. The method of claim 18 wherein the time required for the cutting element to traverse, cut and cauterize tissue is about 1.5 to 4.5 seconds.

23. A bipolar electrosurgical cutting device, comprising:

a handle means for grasping and manipulating the device;

a cutting portion, adjacent to the handle means, having substantially parallel first and second elements that define a tissue engaging space therebetween;

a cutting element disposed within the cutting portion of the device and adapted to be manipulated to sever tissue, the cutting element being electrically isolated from the remainder of the device and being in electrical communication with a remote generator which provides electrosurgical energy to the cutting element for delivery to tissue contacted by the cutting element;

a tissue contacting return electrode provided on a tissue-contacting region of the cutting portion electrically isolated from the cutting element, forming a bipolar electrosurgical device;

means for effecting the movement of the cutting element within the cutting portion of the device to sever tissue; and power control means for activating and regulating the electrosurgical energy supplied to the tool.

24. The device of claim 23 further comprising a pathway disposed within one of the first or second elements which defines a cutting path.

25. The device of claim 23 wherein the first element houses the cutting element and the second element serves as the return electrode.

26. The device of claim 25 further comprising a cartridge means for housing a supply of surgical staples which is disposed within the first element.

27. The device of claim 26 wherein the means for effecting the movement further controls the action of a staple ejecting mechanism such that surgical staples are deployed substantially simultaneously with the cutting movement of the cutting element.

28. The device of claim 27 wherein a means for closing the surgical staples is disposed on the second element.

29. An electrosurgical cutting device, comprising:

a tool housing including a handle portion;

a cutting element, adjacent the handle portion, having substantially parallel first and second elongate tyne elements which define a tissue engaging space therebetween;

a pathway within the first tyne member which defines a cutting path;

a moveable cutting element, electrically isolated from the remainder of the tool, said cutting element being adapted to move from a retracted position through the pathway in the first tyne to sever tissue;

means for moving the cutting element through the pathway to effect cutting of tissue;

a cartridge means for housing a plurality of surgical staples, said cartridge means disposed on the first tyne member, on a side thereof facing the second tyne member and having a longitudinal groove therein to accommodate passage of the cutting element;

a means for deploying the staples substantially simultaneously with the cutting action of the cutting element;

anvil means for effecting closure of the staples, the mandrel means being disposed on a side of the second tyne member facing the first tyne member; and selectively operable electrosurgical current supply means for communicating electrical energy through the cutting element to tissue to cauterize tissue simultaneous with the cutting action of the cutting element.

* * * * *

Disclaimer 5,665,085—Paul C. Nardella, North Easton, Mass. ELECTROSURGICAL CUTTING TOOL. Patent dated September 9, 1997. Disclaimer filed April 30, 1998, by the assignee, Medical Scientific, Inc.

Hereby enters this disclaimer to claims 1, 2, 3, 5 and 9, of said patent.

*(Official Gazette, July 14, 1998)*